(12) United States Patent
Petkov et al.

(10) Patent No.: US 11,883,421 B2
(45) Date of Patent: Jan. 30, 2024

(54) FUNCTIONALIZED SACCHARIDES AS ANTI-INFLAMMATORY AGENTS

(71) Applicant: HUVEPHARMA, Antwerp (BE)

(72) Inventors: Spas Petkov, Antwerp (BE); Veerle Hautekiet, Antwerp (BE)

(73) Assignee: HUVEPHARMA, Antwerp (BE)

(*) Notice: Subject to any disclaimer, the term of this patent is extended or adjusted under 35 U.S.C. 154(b) by 74 days.

(21) Appl. No.: 16/609,714

(22) PCT Filed: May 4, 2018

(86) PCT No.: PCT/EP2018/061510
§ 371 (c)(1),
(2) Date: Oct. 30, 2019

(87) PCT Pub. No.: WO2018/202855
PCT Pub. Date: Nov. 8, 2018

(65) Prior Publication Data
US 2020/0113921 A1    Apr. 16, 2020

(30) Foreign Application Priority Data

May 5, 2017  (EP) .................................. 17169794
May 26, 2017 (EP) .................................. 17173119

(51) Int. Cl.
| | | |
|---|---|---|
| A61K 31/702 | (2006.01) | |
| A61P 29/00 | (2006.01) | |
| A61K 31/7034 | (2006.01) | |
| A61K 31/7028 | (2006.01) | |
| A61P 1/04 | (2006.01) | |
| A23K 20/163 | (2016.01) | |
| A61P 1/00 | (2006.01) | |
| A61K 9/00 | (2006.01) | |

(52) U.S. Cl.
CPC .......... *A61K 31/702* (2013.01); *A23K 20/163* (2016.05); *A61K 9/0056* (2013.01); *A61K 31/7028* (2013.01); *A61K 31/7034* (2013.01); *A61P 1/00* (2018.01); *A61P 1/04* (2018.01); *A61P 29/00* (2018.01)

(58) Field of Classification Search
CPC .............. A61K 31/702; A61K 31/7034; A61K 9/0056; A61P 29/00; A61P 1/00; A23K 20/163
USPC ......................................................... 514/35
See application file for complete search history.

(56) References Cited

U.S. PATENT DOCUMENTS

2007/0161598 A1* 7/2007 Esko ...................... C07H 17/02
536/53
2010/0048492 A1   2/2010 Quesniaux Ryffel et al.

FOREIGN PATENT DOCUMENTS

| FR | 2 908 658 A1 * | 5/2008 |
| FR | 2908658 A1 | 5/2008 |
| KR | 2017031126 A * | 3/2017 |
| WO | 2009046314 A2 | 4/2009 |

OTHER PUBLICATIONS

Tseng et al. (Bioorganic & Medicinal Chemistry Letters 24 (2014) 2412-2414) .*
White et al. (Journal of Inflammation Research 2015:8, 137-147).*
Quesniaux et al.; FR 2 908 658 A1; May 23, 2008 (Machine-English Translation).*
Sauvage et al. (Antibiotics 2016, 5, 12, 1-27).*
Kim et al.; KR 2017031126 A; Mar. 20, 2017 (Machine-English Translation) (Abstract sent).*
Zhang et al. (Int Anesthesiol Clin. 2007; 45(2): 27-37).*
Araki et al., "The Mechanisms Underlying Chronic Inflammation in Rheumatoid Arthritis from the Perspective of the Epigenetic Landscape" Journal of Immunology Research vol. 2016 article ID 6290682, http://dx.doi.org/10.1155/2016/6290682 (Year: 2016).*
Zhao et al., "Inflammation in Chronic Wounds" International Journal of Molecular Sciences vol. 17 p. 2085 doi:10.3390/ijms 17122085 (Year: 2016).*
Holgate et al., "Asthma" Nature Reviews Disease Primers vol. 1 pp. 1-22 doi:10.1038/nrdp.2015.25 (Year: 2015).*
Tian et al., "Pathomechanisms of Oxidative Stress in Inflammatory Bowel Disease and Potential Antioxidant Therapies" Oxidative Medicine and Cellular longevity vol. 2017 Article ID 4535194, 18 pages https://doi.org/10.1155/2017/4535194 (Year: 2017).*
Nathan et al., "Nonresolving Inflammation" Cell vol. 140 pp. 871-882, pp. 871-882 (Year: 2010).*
International Preliminary Report on Patentability dated Nov. 5, 2019, issued in corresponding International Application No. PCT/EP2018/061510, filed May 4, 2018, 1 page.
International Search Report dated Jul. 2, 2018, issued in corresponding International Application No. PCT/EP2018/061510, filed May 4, 2018, 5 pages.
Written Opinion of the International Searching Authority dated Jul. 2, 2018, issued in corresponding International Application No. PCT/EP2018/061510, filed May 4, 2018, 6 pages.
Ainge, G. D. et al., "Phosphatidylinositol mannosides: Synthesis and suppression of allergic airway disease", (14)16: 5632-5642, Aug. 2006.

* cited by examiner

*Primary Examiner* — Eric Olson
(74) *Attorney, Agent, or Firm* — Christensen O'Connor Johnson Kindness PLLC

(57) ABSTRACT

The present invention relates to functionalized saccharides anti-inflammatory agents which acts upon inflammatory mechanisms in mammals, in particular anti-inflammatory agents which act upon the expression of at least one cytokine by suppressing or inhibiting the expression of the at least one cytokine wherein said cytokine is selected from the group consisting of pro-inflammatory cytokines, anti-inflammatory cytokines and chemokines.

10 Claims, No Drawings
Specification includes a Sequence Listing.

FUNCTIONALIZED SACCHARIDES AS ANTI-INFLAMMATORY AGENTS

FIELD OF INVENTION

This present invention relates to functionalized saccharides compounds as anti-inflammatory agents which act upon inflammatory mechanisms in mammals.

BACKGROUND OF THE INVENTION

Inflammation is a complex biological response of the immune system to protect the body against harmful substances, injury and destruction of tissues. The inflammatory response can be triggered by physical, chemical and infectious agents such as bacteria, viruses and other pathogenic microorganisms. The goal of inflammation is to eliminate the initial cause of damage, clear out the damaged cells and tissue, and initiate tissue repair.

Inflammation can be acute or chronic. Acute inflammation refers to the initial response of the body's immune system to harmful stimuli. Chronic inflammation is a form of prolonged inflammation which results in the recruitment of macrophages and T-lymphocytes. Macrophages are large phagocytic white blood cells and together with the T-lymphocytes, known to produce cytokines and enzymes, they cause longer lasting damage to cells. While it is necessary for the body to have a properly functioning immune system, it is as important to keep these inflammatory mechanisms under control, as chronic inflammation can give rise to a variety of pathologies and even cancer.

Inflammation is however not a synonym for infection. Infection relates merely to the interaction of the invasion of a microorganism with the body's inflammatory response to that invasion. Inflammation on the other hand describes the inflammatory mechanism taking place irrespectively of the causal agent. Notwithstanding in healthcare, inflammation or an organ specific inflammation denoted with the suffix -itis, is often referred to as an infection because microbial invasion is commonly observed in correlation with inflammation. It is nevertheless important to discriminate between the two since many pathological conditions involve inflammatory processes which are not driven by microbial or viral invasion and the other way around not all microbial or viral infections will result in inflammation.

The confusion between infection and inflammation is especially existent for gastritis or the presence of inflammation in the stomach. Many clinicians consider chronic gastritis equivalent with *Helicobacter pylori* (*H. pylori*) infection. It is however known that there are numerous other causes for the condition. Moreover, gastric pathology also can be persistent even after the successful eradication of *H. Pylori*. In the American Journal of Gastroenterology, Genta et al. have very recently reported that in up to 20% of the patients who received a gastric biopsy, a diagnosis of *Helicobacter*-negative gastritis was made. Given its common occurrence, Börkman et al. have published a proposal in the New England Journal Of Medicine to consider *Helicobacter*-negative gastritis as a separate clinical entity. Known causes of gastric inflammation without bacterial infection, in particular *H. pylori* infection, include:
  (i) viral infection (*Cytomegalovirus, Herpes simplex*)
  (ii) chemical or reactive inflammation caused by a bile and pancreatic juice reflux to the stomach or by exogenous substances such as NSAIDs (Non-Steroidal Anti-Inflammatory Drugs), ASA (Acetylsalicylic Acid), alcohol or chemotherapeutics
  (iii) autoimmune inflammation characterized by the presence of antibodies against parietal cells
  (iv) post-radiation and eosinophilic inflammation
  (v) inflammation in the course of collagenosis
  (vi) inflammation in the course of crohn's disease
  (vii) inflammation in the course of sarcoidosis
  (viii) stress-induced inflammation
  (ix) gastric non-*H. pylori Helicobacter* (NHPH) species in humans, of which *H. Suis* is the most prevalent. It is associated with chronic gastritis, gastric ulceration and other gastric pathological changes in both animals as humans (G. Zhang et al., Vet Res (2016) 47:101, p. 1 I. 1-3).
  (x) idiopathic: all cases of gastritis where no causal factor can be identified.

In addition to the problem of *Helicobacter*-negative gastritis, the recurrence of gastric ulcers, even after successful eradication of *Helicobacter* species, remains a challenge in human medicine as well as in livestock farming. In the case of swines for example, though treated swines may heal, the recurrence of ulcers is a common problem. The recurrence of ulcers will result in animal discomfort and loss of appetite with weight loss and economical implications as a result. But also in human medicine the recurrence of gastric ulcers represents a significant health burden. Currently those suffering from chronic gastritis and/or gastric ulcer disease are dependent on the long-term use of Proton Pump Inhibitors (PPI's) to block acid formation in the stomach. Said long term use is known to have many side-effects and confers an increased risk of chronic kidney disease, kidney failure, and an increased risk of cardiovascular events.

Alternatively, instead of blocking acid production in the stomach gastric ulcers and gastritis are treated by directly targeting the *Helicobacter pylori* bacteria.

In addition, the use of NSAIDs is contra-indicated to temper gastric inflammation, as these drugs are known to be a risk factor for gastric pathology.

In view of the above there is a need for anti-inflammatory agents which may overcome the disadvantages of the current anti-inflammatory treatments such as the many side-effects, i.e. an increased risk of chronic kidney disease, kidney failure, an increased risk of cardiovascular events and the like, limited domain of application, compliance failure and which overcome the problem of recurrence of ulcers, in particular gastric ulcers.

SUMMARY OF THE INVENTION

The Applicant has now surprisingly found that it is possible to provide anti-inflammatory agents fulfilling the above mentioned needs.

It is an objective of the present invention to provide an alternative anti-inflammatory agent instead of NSAIDs to suppress inflammation in the stomach of mammals suffering from gastritis, gastric ulcers or those at risk of developing them.

It is an objective of the present invention to provide an alternative to the long-term use of Proton Pump Inhibitors (PPI's) in subjects suffering from gastric ulcer disease and chronic gastritis.

It is an objective of the present invention to provide an anti-inflammatory agent which can act upon the mechanisms of inflammation underlying gastric ulcer disease and gastritis in mammals.

The present invention relates to compounds for use as an anti-inflammatory agent which act upon inflammatory mechanisms in mammals [anti-inflammatory compound (C), herein after], wherein said anti-inflammatory compound (C) is at least one of the compounds according to general formulae (I), (II), (III) or (IV), or the pharmaceutically acceptable salt, pharmaceutically acceptable solvate, isomer or mixture thereof:

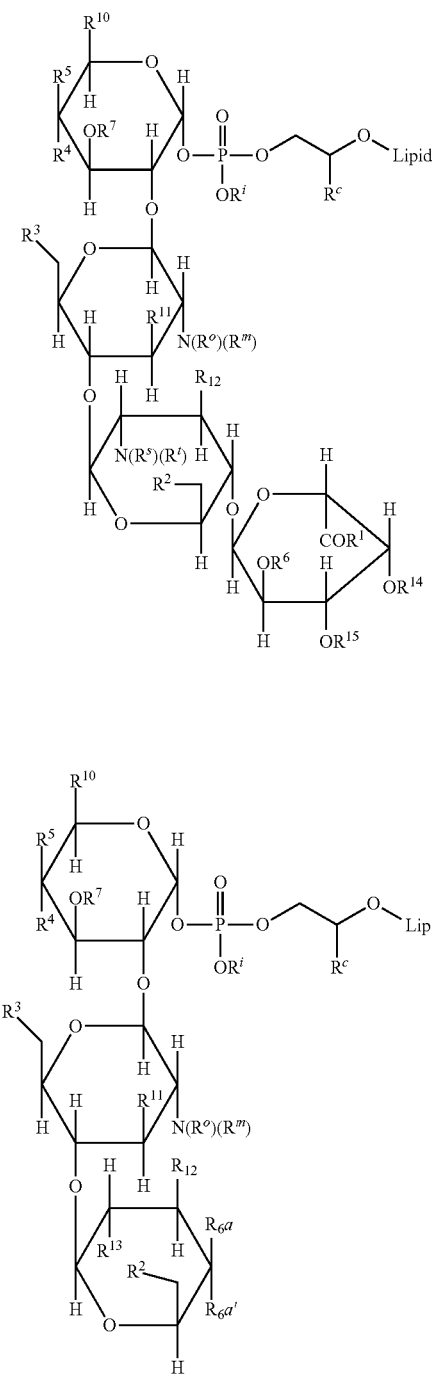

formula (I)

formula (II)

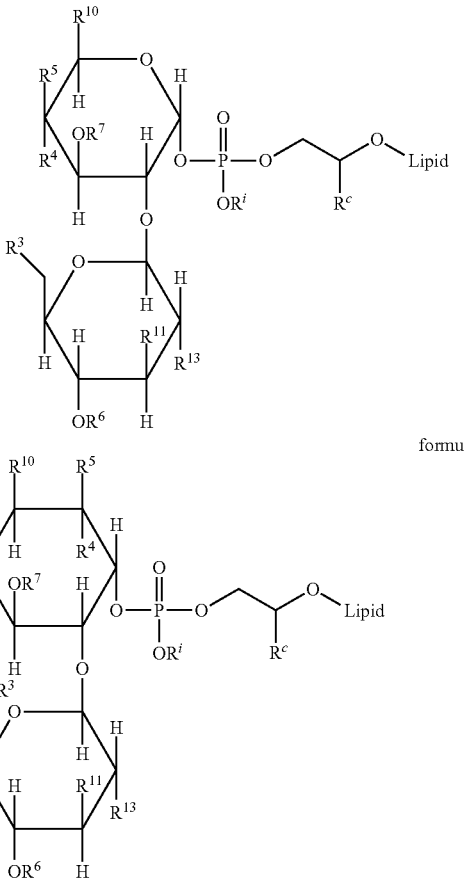

formula (III)

formula (IV)

wherein
each of $R^1$ is independently selected from —OH or —N($R^{1a}$)($R^{1b}$), wherein each of $R^{1a}$ and $R^{1b}$, independently from each other and at each occurrence, are selected from the group consisting of H, an amino protecting group, aryl, heteroaryl, aliphatic and a heteroaliphatic group, each of $R^2$, $R^4$, $R^5$, $R^{11}$ and $R^{12}$, independently from each other and at each occurrence, are selected from the group consisting of H, —$OR^z$, —N($R^z$)$_2$, aryl, heteroaryl, aliphatic, and a heteroaliphatic group, wherein $R^z$ is independently selected from the group consisting of H, an hydroxyl protecting group, an amino protecting group, aryl, heteroaryl, aliphatic, heteroaliphatic and a carbohydrate moiety, each of $R^3$ is independently selected from the group consisting of H, —OH, —$NH_2$, —SH, $OR^w$, —NH($R^w$), —N($R^w$)$_2$, —$SR^w$, —O(C=O)$R^w$, —NH(C=O)$R^w$, —O(C=NH)$R^w$, —NH(C=NH)$R^w$, —S(C=NH))$R^w$, —NH(C=S)$R^w$, —S(C=O)$R^w$, —O(C=S)$R^w$, —S(=S)$R^w$, aryl, heteroaryl, aliphatic and a heteroaliphatic group, wherein $R^w$ is selected from the group consisting of a carbohydrate moiety, aryl, heteroaryl, aliphatic, and heteroaliphatic group, each of $R^6$, $R^{14}$ and $R^{15}$, independently from each other and at each occurrence are selected from the group consisting of H, hydroxyl protecting group, aryl, heteroaryl, aliphatic, heteroaliphatic group and carbohydrate moiety, each of $R^7$ is independently selected from the group consisting of H, $C(=O)N(R^{z'})_2$, $-C(=O)OR^{z'}$, an hydroxyl protecting group, aryl, heteroaryl, aliphatic, heteroaliphatic group and carbohydrate moiety, wherein $R^{z'}$ is independently selected from the group consisting of H, an hydroxyl protecting group, an amino protecting group, aryl, heteroaryl, aliphatic, and a heteroaliphatic group, each of $R^{10}$ is independently selected from the group consisting of $-C(=O)N(R^l)(R^p)$, $-C(=O)OR^k$, and $-CH_2OR^k$, wherein $R^l$ and $R^p$ are independently from each other and at each occurrence selected from the group consisting of H, an amino protecting group, aryl, heteroaryl, aliphatic, heteroaliphatic group and a carbohydrate moiety, wherein $R^k$ is independently selected from the group consisting of H, an hydroxyl protecting group, aryl, heteroaryl, aliphatic, heteroaliphatic group and a carbohydrate moiety, each of $R^{13}$ is independently selected from the group consisting of —OH and $-N(R^{o''})(R^{m''})$, wherein $R^{o''}$ and $R^{m''}$ independently from each other and at each occurrence, are selected from the group consisting of H, $-C(=O)R^h$, an amino protecting group, aryl, heteroaryl, aliphatic and heteroaliphatic group, wherein $R^h$ is selected from the group consisting of a carbohydrate moiety, aryl, heteroaryl, aliphatic and heteroaliphatic group, each of $(R^o)$ and $(R^m)$, independently from each other and at each occurrence, are selected from the group consisting of H, $-C(=O)R^{w'}$, an amino protecting group, aryl, heteroaryl, aliphatic and heteroaliphatic group, wherein $R^{w'}$ is selected from the group consisting of a carbohydrate moiety, aryl, heteroaryl, aliphatic and heteroaliphatic group;

each of $(R^s)$ and $(R^t)$, independently from each other and at each occurrence are selected from the group consisting of H, $-C(=O)R^{w''}$, an amino protecting group, aryl, heteroaryl, aliphatic and heteroaliphatic group, wherein $R^{w''}$ is selected from the group consisting of a carbohydrate moiety, aryl, heteroaryl, aliphatic and heteroaliphatic group;

each of $R^{6a}$ and $R^{6a'}$, independently from each other and at each occurrence are selected from H or —OH, preferably $R^{6a}$ is H and $R^{6a'}$ is —OH;

each of $R^c$ is independently selected from the group consisting of H, halogen, heteroaryl, $-OR^q$, $-N(R^q)_2$, $-SR^q$, $NO_2$, $-NC$, $-CN$, $-N_3$, $-N(R^q)=NR^q$, $-CHO$, $-C(=O)R^q$, $-C(=S)R^q$, $C(=NR^q)R^q$, $-C(=O)OR^q$, $-C(=NR^q)OR^q$, $-C(=NR^q)N(R^q)_2$, $-C(=O)N(R^q)_2$, $-C(=S)OR^q$, $-C(=O)SR^q$, $-C(=S)SR^q$, $-P(=O)(OR^q)_2$, $-S(=O)(OR^q)$, $-S(=O)_2(OR^q)$, $-P(=O)N(R^q)_2$, $-P(=O)_2N(R^q)_2$, $-C(=O)NR'S(=O)_2R^q$, $-S(=O)N(R^q)_2$ and $-S(=O)_2N(R^q)_2$, wherein each of $R^q$ is independently selected from the group consisting of H, aliphatic, heteroaliphatic, aryl, heteroaryl, and an hydroxyl protecting group, each of $R^i$ is independently selected from the group consisting of H, an hydroxyl protecting group, aliphatic, heteroaliphatic, aryl, and heteroaryl, each Lipid is independently selected from H or a $C_{1-30}$ aliphatic moiety, wherein 0 to 10 methylene units are optionally replaced with —O—, $-NR^x-$, —S—, $-C(=O)-$, $-C(=NR^x)-$, $-S(=O)-$, $-S(=O)_2-$, $-N=N-$, $-C=N-$, $-C(R^y)=C(R^{y'})-$, $-N-O-$, an arylene, or an heteroarylene moiety, wherein each of $R^x$ is independently selected from the group consisting of H, aliphatic, heteroaliphatic, aryl, heteroaryl, or an amino protecting group, and wherein each of $R^y$ and $R^{y'}$, independently from each other and at each occurrence are selected from the group consisting of H, aliphatic, heteroaliphatic, aryl and heteroaryl group.

The present invention further relates to a pharmaceutical composition for use as an anti-inflammatory agent which acts upon inflammatory mechanisms in mammals comprising a carrier, and as active ingredient an effective amount of the anti-inflammatory compound (C) as defined in any one of the embodiments presented herein.

The present invention further relates to a process of preparing said pharmaceutical composition.

The present invention further relates to the anti-inflammatory compound (C), as defined in any one of the embodiments presented herein, for use as a medicament.

The present invention further relates to a pharmaceutical composition comprising a carrier, and as active ingredient an effective amount of the anti-inflammatory compound (C) as defined in any one of the embodiments presented herein, for use as a medicament.

The present invention further relates to the anti-inflammatory compound (C), as defined in any one of the embodiments presented herein, for use in the treatment of inflammatory diseases or inflammatory-related diseases.

The present invention further relates to the anti-inflammatory compound (C), as defined in any one of the embodiments presented herein, for use in the treatment of a disease mediated by at least one cytokine.

The present invention further relates to an in-vivo method of suppressing or inhibiting inflammatory responses by using the anti-inflammatory compound (C), as defined in any one of the embodiments presented herein.

The present invention further relates to a method of suppressing or inhibiting the expression of at least one cytokine in a mammal.

The present invention further relates to a method of treating inflammatory-related diseases associated with cytokine expression levels in mammals.

Anti-Inflammatory Compound (C), and
Pharmaceutically Acceptable Salt Thereof

It is further understood that all definitions and preferences as described for the anti-inflammatory compound (C) above equally apply for this embodiment and all further embodiments, as described below.

As used in the foregoing and hereinafter, the following definitions apply unless otherwise noted.

The term "aliphatic" includes both saturated and unsaturated, nonaromatic, straight chain (i.e., unbranched), branched, acyclic, and cyclic hydrocarbon chain having 1 to 30 carbon atoms, which are optionally substituted with one or more groups including but not limited to alkyl, alkynyl, alkenyl, aryl, halide, nitro, amino, ester, ketone, aldehyde, hydroxy, carboxylic acid, or alkoxy. According to certain embodiments, as used herein, $C_{F-G}$ aliphatic defines a $C_{F-G}$ aliphatic group having F to G carbon atoms, e.g. $C_{1-12}$ aliphatic defines an aliphatic group containing 12 carbon atoms, $C_{1-10}$ aliphatic defines an aliphatic group containing 1 to 10 carbon atoms.

As will be appreciated by one of ordinary skilled in the art, "aliphatic" is intended herein to include, but is not limited to alkyl, alkenyl, and alkynyl moieties. As used herein the term "alkyl" "alkenyl", and "alkynyl" have the broadest meaning generally understood in the art, and may include a moiety which is linear, branched, cyclic (cycloalkyl, cycloalkenyl, cycloalkynyl) or a combination thereof.

The term "alkyl", alone or in combination means an alkane-derived radical, which may be a straight chain alkyl, branched alkyl or cyclic alkyl, containing from 1 to 30 carbon atoms, unless otherwise specified. The straight chain or branched alkyl group is attached at any available point to produce a stable compound. Alkyl also includes a straight chain or branched alkyl group that contains or is interrupted by a cycloalkyl portion. According to certain embodiments $C_{A-B}$ alkyl defines a straight or branched alkyl radical having from A to B carbon atoms, e.g. $C_{1-15}$ alkyl defines a straight or branched alkyl radical having from 1 to 15 carbon atoms, $C_{1-12}$ alkyl defines a straight or branched alkyl radical having from 1 to 12 carbon atoms, $C_{1-6}$ alkyl defines a straight or branched alkyl radical having from 1 to 6 carbon atoms such as for example methyl, ethyl, 1-propyl, 2-propyl, l-butyl, 2-butyl, 2-methyl-1-propyl. According to certain embodiments a cyclic $C_{C-D}$ alkyl defines a cyclic alkyl radical having from C to D carbon atoms, e.g. $C_{3-6}$ cyclic alkyl.

The term "alkenyl", alone or in combination, means a straight or branched hydrocarbon containing 1-30 carbon atoms, unless otherwise specified and at least one carbon to carbon double bond. Examples of alkenyl groups include ethenyl, propenyl, isopropenyl, butenyl, cyclohexenyl, cyclohexenylalkyl and the like. Alkenyl also includes a straight chain or branched alkenyl group that contains or is interrupted by a cycloalkyl portion. Carbon to carbon double bonds may be either contained within a cycloalkyl portion or within a straight chain or branched portion. According to certain embodiments $C_{H-I}$ alkenyl defines a straight or branched alkenyl radical having from H to I carbon atoms, e.g. $C_{1-6}$ alkenyl defines a straight or branched alkenyl radical having from 1 to 6 carbon atoms.

The term "alkynyl" alone or in combination means a straight, branched or cyclic hydrocarbon containing 1 to 30 carbon atoms containing at least one carbon to carbon triple bond. Examples of alkynyl groups include ethynyl, propynyl, butynyl and the like.

As used herein, the term "heteroaliphatic," refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons having 1 to 30 carbon atoms, unless speficied otherwise, which are optionally substituted with one or more groups, including but not limited to alkyl, alkynyl, alkenyl, aryl, halide, nitro, amino, ester, ketone, aldehyde, hydroxy, carboxylic acid, or alkoxy and that contain one or more hetero atoms such as oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skilled in the art, "heteroaliphatic" is intended herein to include heteroalkyl, heterocycloalkyl, heterocycloalkenyl, and heterocycloalkynyl moieties. Thus, as used herein, the term "heteroalkyl" includes straight, branched and cyclic alkyl groups that contain one or more one or more hetero atoms such as oxygen, sulfur, nitrogen, phosphorus, or silicon atoms, e.g., in place of carbon atoms. An analogous convention applies to other generic terms such as "heteroalkenyl", "heteroalkynyl", and the like. Furthermore, as used herein, the terms "heteroalkyl", "heteroalkenyl", "heteroalkynyl", and the like encompass both substituted and unsubstituted groups.

As used herein, the term "aryl", alone or in combination means any carbon-based aromatic group including, but not limited to, phenyl, tolyl, xylyl, cumenyl, naphthyl, anthracenyl etc., optionally carbocyclic fused with a cycloalkyl or heterocyclyl of preferably 5-7, more preferably 5-6, ring members and/or optionally substituted with 1 to 5 groups or substituent. An aryl may be optionally substituted with one or more groups including but not limited to alkyl, alkynyl, alkenyl, aryl, halide, nitro, amino, ester, ketone, aldehyde, hydroxy, carboxylic acid, or alkoxy whereby the substituent is attached at one point to the aryl or whereby the substituent is attached at two points to the aryl to form a bicyclic system e.g. benzodioxole, benzodioxan, benzimidazole.

The term "heteroaryl", alone or in combination means a monocyclic aromatic ring structure containing 5 or 6 ring atoms, or a bicyclic aromatic group having 8 to 10 atoms, containing one or more, preferably 1-4, more preferably 1-3, heteroatoms independently selected from the group O, S, and N, and optionally substituted with 1 to 5 groups or substituents including but not limited alkyl, alkynyl, alkenyl, aryl, halide, nitro, amino, ester, ketone, aldehyde, hydroxy, carboxylic acid, or alkoxy Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. More specifically the term heteroaryl includes, but is not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like.

According to a certain embodiment of the present invention, the Lipid is an unsaturated $C_{4-20}$ hydrocarbon chain, wherein 1 to 10 methylene units are replaced by —C(R$^y$)=C(R$^{y'}$)— wherein each of R$^y$ and R$^{y'}$, independently from each other and at each occurrence, are selected from the group consisting of H, aliphatic, heteroaliphatic, aryl, or heteroaryl; and wherein said hydrocarbon chain is optionally substituted with a $C_{1-6}$ alkyl, a $C_{3-6}$ cyclic alkyl, $C_{1-6}$ alkenyl or hydroxyl group, preferably the Lipid is a $C_{4-20}$ hydrocarbon chain, wherein 1 to 5 methylene units are replaced by —C(R$^y$)=C(R$^{y'}$)— wherein each of R$^y$ and R$^{y'}$, independently from each other and at each occurrence, are selected from the group consisting of H, $C_{1-6}$ alkyl and $C_{1-6}$ alkenyl and wherein said hydrocarbon chain is optionally substituted with a $C_{1-6}$ alkyl, a $C_{3-6}$ cyclic alkyl, $C_{1-6}$ alkenyl or hydroxyl group, more preferably the Lipid is chosen among following formulae:

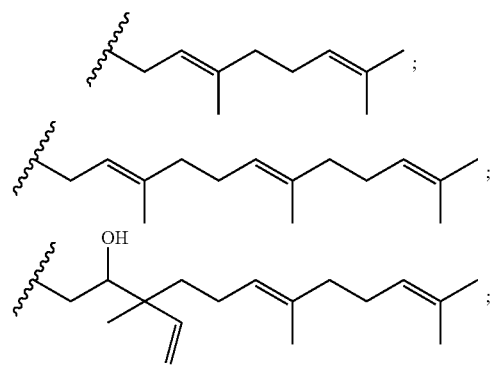

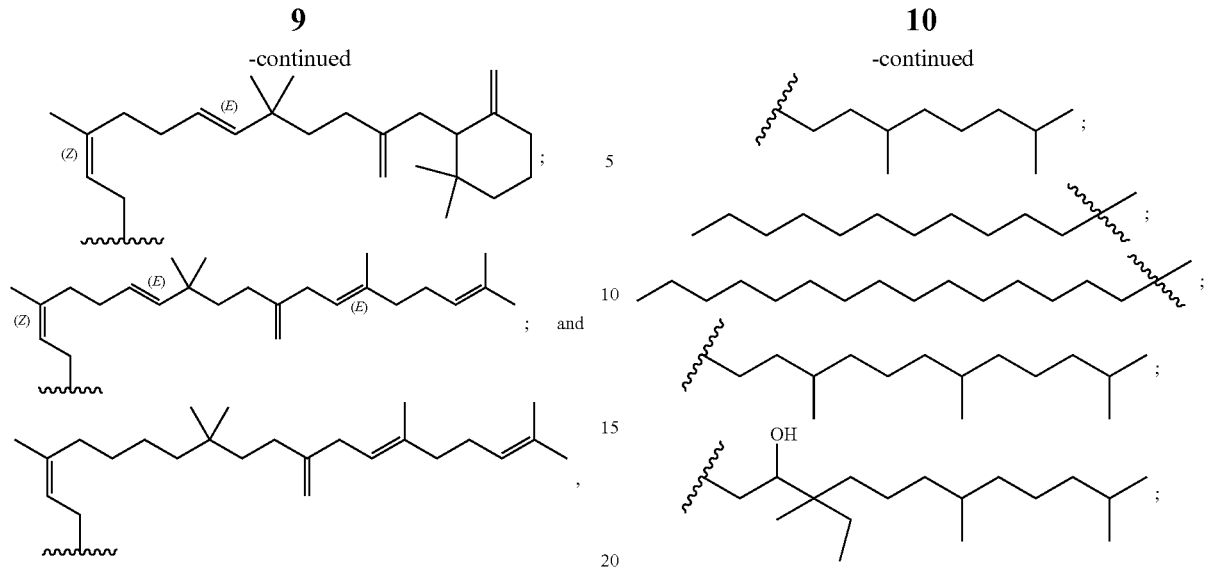

Even more preferred, the Lipid is chosen among following formulae:

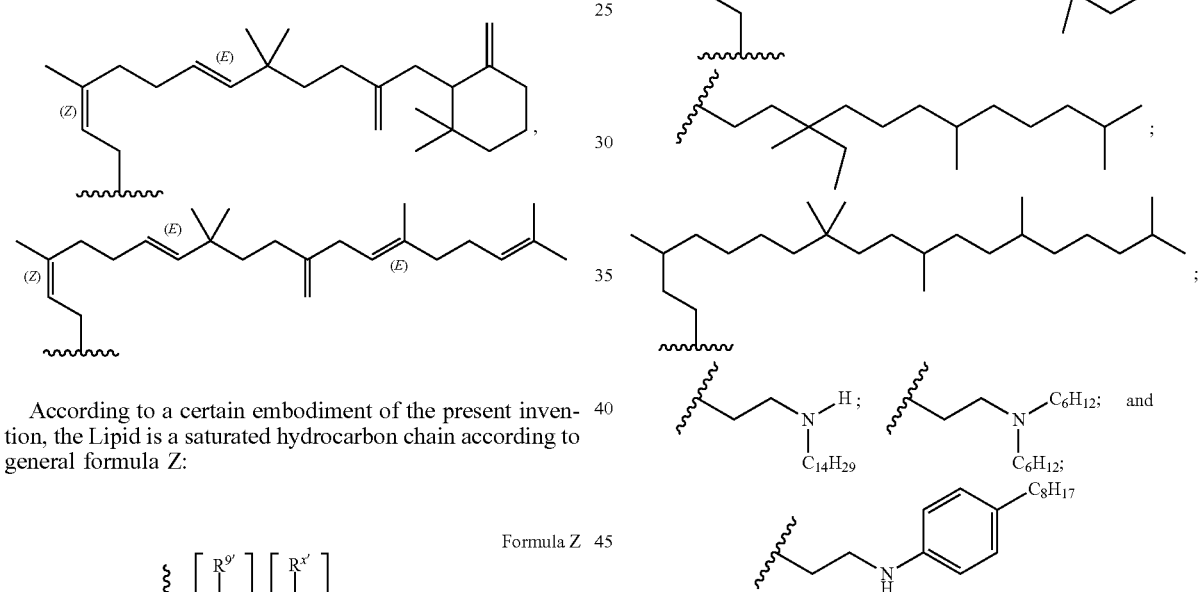

According to a certain embodiment of the present invention, the Lipid is a saturated hydrocarbon chain according to general formula Z:

$$\left[\begin{array}{c} R^{9'} \\ | \\ -C- \\ | \\ R^{9''} \end{array}\right]_n \left[\begin{array}{c} R^{x'} \\ | \\ -N- \\ | \\ R^{x''} \end{array}\right]_m \quad \text{Formula Z}$$

wherein
each of $R^{9'}$ and $R^{9''}$ are independently from each other and at each occurrence selected from the group consisting of H, —OH and $C_{1-6}$ alkyl,
each of $R^{x'}$ and $R^{x''}$, independently from each other and at each occurrence, are selected from H, a $C_{1-15}$ alkyl and an aryl wherein said aryl is optionally further substituted by a $C_{1-15}$ alkyl, and wherein n=4 to 30, and m=0 or 1

Preferably, the saturated hydrocarbon chain is chosen among following formulae:

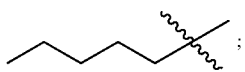

According to a certain embodiment of the present invention, $R^1$ is independently selected from —OH or —N($R^{1a}$)($R^{1b}$) wherein each of $R^{1a}$ and $R^{1b}$, independently from each other and at each occurrence, are selected from the group consisting of H, $C_{1-20}$ aliphatic and $C_{1-20}$ heteroaliphatic group, preferably $R^1$ is OH, $NH_2$, or NH($R^{1b}$), wherein R1b is a $C_{1-10}$ cycloalkyl group or $C_{1-10}$ cycloalkenyl which is optionally substituted with an halide, hydroxyl or alkoxy, more preferably $R^1$ is —NH($R^{1b}$), wherein $R^{1b}$ is of following formula:

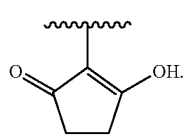 [SMILES: *C1=C(O)CCC1=O]

According to a certain embodiment of the present invention, $R^3$ is independently selected from the group consisting of H, —OH and —$OR^w$, wherein $R^w$ is selected from the group consisting of a carbohydrate moiety, wherein said carbohydrate moiety is independently selected from the group consisting of D- and L-monosaccharides, such as notably D-erythrose, L-erythrose, D-threose, L-threose, L-erythrulose, D- erythrulose, D-arabinose, L-arabinose, D-deoxyribose, L-deoxyribose, D-lyxose, L-lyxose, D-ribose, L-ribose, D-ribulose, L-ribulose, D-xylose, L-xylose, D-xylulose, L-xylulose, D-allose, L- allose, D-altrose, L-altrose, D-galactose, L-galactose, D-glucose, L-glucose, D-gulose, L-gulose, D-idose, L-idose, D-mannose, L-mannose, D-talose, L-talose, D-fructose, L-fructose, D-psicose, L-psicose, D-sorbose, L-sorbose, D-tagatose, L-tagatose, D-fucose, L-fucose, D-rhamnose and L-rhamnose, disaccharides, such as notably sucrose, lactose, trehalose, and maltose, trisaccharides such as notably acarbose, raffinose, and melezitose, more preferably, $R^3$ is —$OR^w$, wherein $R^w$ is a D-monosaccharide such as notably D-erythrose, D-threose, D- erythrulose, D-arabinose, D-deoxyribose, D-lyxose, D-ribose, D-ribulose, D-xylose, D-xylulose, D-allose, D-altrose, D-galactose, D-glucose, D-gulose, D-idose, D-mannose, D-talose, D-fructose, D-psicose, D-sorbose, D-tagatose, D-fucose, and D-rhamnose, even more preferably, $R^3$ is —$OR^w$, wherein $R^w$ is independently selected from the group consisting of D-glucose, D-galactose, D-allose, D-altrose, D-mannose, D-iodose, D-galose or D-talose, most preferably, $R^3$ is —$OR^w$, wherein $R^w$ is D-glucose.

According to a certain embodiment of the present invention, each of $R^2$, $R^4$, $R^5$, $R^{11}$ and $R^{12}$, independently from each other and at each occurrence, are selected from the group consisting of H, $OR^z$, a $C_{1-12}$ aliphatic, $C_{1-12}$ heteroaliphatic and a carbohydrate moiety, wherein RZ is selected from the group consisting of H, hydroxyl protecting group, $C_{1-12}$ aliphatic, $C_{1-12}$ heteroaliphatic, aryl and heteroaryl, and wherein said carbohydrate moiety is selected from the group consisting of D-monosaccharides such as notably D-erythrose, D-threose, D- erythrulose, D-arabinose, D-deoxyribose, D-lyxose, D-ribose, D-ribulose, D-xylose, D-xylulose, D-allose, D-altrose, D-galactose, D-glucose, D-gulose, D-idose, D-mannose, D-talose, D-fructose, D-psicose, D-sorbose, D-tagatose, D-fucose, and D-rhamnose, preferably each $R^2$, $R^4$, $R^5$, $R^{11}$ and $R^{12}$, independently from each other and at each occurrence, are selected from the group consisting of H, $OR^z$, a hydroxyl protecting group, $C_{1-6}$ alkyl and a carbohydrate moiety, wherein $R^z$ is selected from the group consisting of H, a hydroxyl protecting group and $C_{1-6}$ alkyl, and wherein said carbohydrate moiety is selected from the group consisting of D-glucose, D-galactose, D-allose, D-altrose, D-mannose, D-iodose, D-galose and D-talose, more preferably $R^2$, $R^4$, $R^{11}$ and $R^{12}$, independently from each other and at each occurrence, are selected from H or $OR^z$, wherein $R^z$ is selected from H or $C_{1-6}$ alkyl, more preferably $R^5$ is a $C_{1-6}$ alkyl, even more preferably $R^2$ is H, $R^4$, $R^{11}$ and $R^{12}$ are —OH and $R^5$ is —$CH_3$;

According to a certain embodiment of the present invention, each of $R^6$, $R^{14}$, and $R^{15}$, independently from each other and at each occurrence, are selected from the group consisting of H, hydroxyl protecting group, $C_{1-12}$ aliphatic and $C_{1-12}$ heteroaliphatic group, preferably $R^6$, $R^{14}$ and $R^{15}$, independently from each other and at each occurrence, are selected from the group consisting of H or an hydroxyl protecting group, more preferably $R^6$, $R^{14}$ and $R^{15}$, independently from each other and at each occurrence, are H.

According to a certain embodiment of the present invention, $R^7$ is —C(=O)N($R^{z'}$)$_2$ group, wherein each of $R^{z'}$ is independently selected from the group consisting of $R^{z'}$ is selected from the group consisting of H, aryl, heteroaryl and $C_{1-12}$ alkyl, preferably each of $R^{z'}$ is independently selected from H or $C_{1-12}$ alkyl, more preferably each of $R^{z'}$ is independently selected from the group consisting of H, methyl, ethyl and propyl, most preferably each of $R^{z'}$ is independently H.

According to a certain embodiment of the present invention, each of $R^{10}$ is independently selected from —C(=O)N($R^l$)($R^p$) or —C(=O)$OR^k$, wherein $R^l$ and $R^p$ are independently from each other and at each occurrence, selected from the group consisting of H, an amino protecting group, aryl, heteroaryl, $C_{1-12}$ aliphatic and $C_{1-12}$ heteroaliphatic group, and wherein $R^k$ is independently selected from the group consisting of H, an hydroxyl protecting group, aryl, heteroaryl, $C_{1-30}$ aliphatic and $C_{1-30}$ 30 heteroaliphatic group, preferably each of $R^{10}$ is independently selected from —C(=O)N($R^l$)($R^p$) or —C(=O)$OR^k$, wherein $R^l$ and $R^p$ are independently from each other and at each occurrence, selected from the group consisting of H, an amino protecting group, aryl, heteroaryl and $C_{1-6}$ alkyl, wherein each of $R^k$ is independently selected from the group consisting of H, an hydroxyl protecting group and $C_{1-6}$ alkyl, more preferably, each of $R^{10}$ is independently selected from —C(=O)N($R^l$)($R^p$) or —C(=O)$OR^k$, wherein $R^l$ and $R^p$, independently from each other and at each occurrence, are selected from the group consisting of H, an amino protecting group, methyl, ethyl, and propyl, wherein each of $R^k$ is independently selected from the group consisting of H, an hydroxyl protecting group, methyl, ethyl, and propyl, most preferably, $R^{10}$ is —C(=O)$NH_2$ or —C(=O)OH.

According to a certain embodiment of the present invention, each of $R^{13}$ is independently selected from the group consisting of —OH and —N($R^{o''}$)($R^{m''}$), wherein $R^{o''}$ and $R^{m''}$, independently from each other and at each occurrence, are selected from the group consisting of H, —C(=O)$R^h$, an amino protecting group, $C_{1-12}$ aliphatic and $C_{1-12}$ heteroaliphatic group, wherein $R^h$ is independently selected from a $C_{1-12}$ aliphatic or $C_{1-12}$ heteroaliphatic group, preferably, $R^{o''}$ and $R^{m'}$, independently from each other and at each occurrence, are selected from the group consisting of H, —C(=O)$R^h$ and $C_{1-12}$ alkyl, wherein $R^h$ is $C_{1-12}$ alkyl, more preferably $R^{o''}$ and $R^{m''}$, independently from each other and at each occurrence, are selected from the group consisting of H, —C(=O)$R^h$ and $C_{1-6}$ alkyl, wherein $R^h$ is $C_{1-6}$ alkyl, most preferably $R^{o''}$ is H and $R^{m'}$ is —C(=O)$CH_3$.

According to a certain embodiment of the present invention, each of ($R^o$) and ($R^m$), independently from each other and at each occurrence, are selected from the group consisting of H, —C(=O)$R^{w'}$, an amino protecting group, $C_{1-12}$ aliphatic and $C_{1-12}$ heteroaliphatic group, wherein $R^{w'}$ is independently selected from the group consisting of a $C_{1-12}$ aliphatic and $C_{1-12}$ heteroaliphatic group, preferably ($R^o$) and ($R^m$), independently from each other and at each occurrence, are selected from the group consisting of H, —C(=O)$R^{w'}$, an amino protecting group and $C_{1-12}$ alkyl, wherein $R^{w'}$ is a $C_{1-12}$ alkyl, more preferably ($R^o$) and ($R^m$), independently from each other and at each occurrence, are selected from the group consisting of H, —C(=O)$R^{w'}$, and $C_{1-6}$ alkyl, wherein $R^{w'}$ is a $C_{1-6}$ alkyl, most preferably ($R^o$) is H and ($R^m$) is —C(=O)$CH_3$.

According to a certain embodiment of the present invention, each of ($R^s$) and ($R^t$), independently from each other and at each occurrence are selected from the group consisting of H, —C(=O)R$^{w''}$, an amino protecting group, C$_{1-12}$ aliphatic and C$_{1-12}$ heteroaliphatic group, wherein R$^{w''}$ is independently selected from a C$_{1-12}$ aliphatic or C$_{1-12}$ heteroaliphatic group, preferably (R$^s$) and (R$^t$), independently from each other and at each occurrence, are selected from the group consisting of H, —C(=O)R$^{w''}$, an amino protecting group and C$_{1-12}$ alkyl, wherein R$^{w''}$ is C$_{1-12}$ alkyl, more preferably (R$^s$) and (R$^t$), independently from each other and at each occurrence, are selected from the group consisting of H, —C(=O)R$^{w''}$, and C$_{1-6}$ alkyl, wherein R$^{w''}$ is C$_{1-6}$ alkyl, most preferably (R$^s$) is H and (R$^t$) is —C(=O)CH$_3$.

According to a certain embodiment of the present invention, each of R$^c$ is independently selected from the group consisting of H, —C(=O)OR$^q$, —C(=O)SR$^q$, —C(=S)OR$^q$, —C(=O)SR$^q$, —C(=S)SR$^q$, wherein each of R$^q$ is independently selected from the group consisting of H, C$_{1-12}$alkyl, aryl, heteroaryl and an hydroxyl protecting group, preferably each of R$^c$ is independently selected from the group consisting of H, —C(=O)OR$^q$, —C(=O)SR$^q$, and —C(=O)SR$^q$, wherein each of R$^q$ is independently selected from the group consisting of H, C$_{1-6}$ alkyl and an hydroxyl protecting group, more preferably each of R$^c$ is independently selected from H or —C(=O)OR$^q$, wherein each of R$^q$ is independently selected from the group consisting of H, methyl, ethyl and propyl, most preferably R$^c$ is —C(=O)OH.

According to a certain embodiment of the present invention, each of R$^i$ is independently selected from the group consisting of H, an hydroxyl protecting group, C$_{1-12}$ aliphatic, C$_{1-12}$ heteroaliphatic, aryl and heteroaryl, preferably R$^i$ is independently selected from the group consisting of H, an hydroxyl protecting group, C$_{1-12}$ alkyl, aryl and heteroaryl, more preferably R$^i$ is independently selected from the group consisting of H, an hydroxyl protecting group and C$_{1-6}$ alkyl, even more preferably R$^i$ is independently selected from the group consisting of H, an hydroxyl protecting group, methyl, ethyl, and propyl, most preferably R$^i$ is H.

The anti-inflammatory compounds (C) of the present invention, as detailed above, have several centers of chirality and exist as stereochemically isomeric forms. The term "stereochemically isomeric forms" as used herein defines all the possible compounds made up of the same atoms bonded by the same sequence of bonds but having different three-dimensional structures which are not interchangeable, which the anti-inflammatory compound (C) as specified herein, may possess.

Unless otherwise mentioned or indicated, the chemical designation of the anti-inflammatory compounds (C), as detailed above, encompasses the mixture of all possible stereochemically isomeric forms, which said anti-inflammatory compounds (C) may possess. Said mixture may contain all diastereomers and/or enantiomers of the basic molecular structure of said anti-inflammatory compounds (C). All stereochemically isomeric forms of the compounds of the present invention both in pure form or mixed with each other are intended to be embraced within the scope of the present invention.

Preferred anti-inflammatory compounds (C) are compounds according to formula (Ia) [anti-inflammatory compounds (C) of class I, herein after] or the pharmaceutically acceptable salt, pharmaceutically acceptable solvate, isomer or mixture thereof,

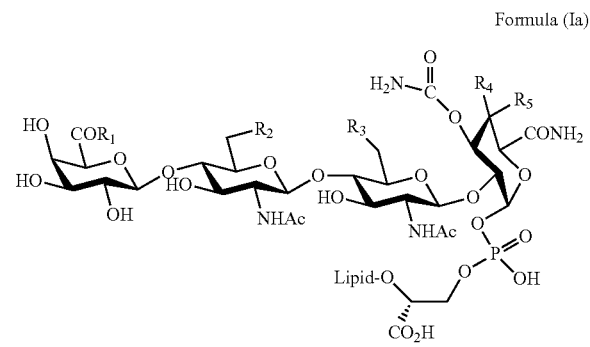

Formula (Ia)

wherein
each of R$^1$ is independently selected from OH, NH$_2$, or NH(R$^{1b}$), wherein R1b is a C1-10 cycloalkyl group or C1-10 cycloalkenyl which is optionally substituted with an halide, hydroxyl or alkoxy, more preferably R1 is —NH(R$^{1b}$), wherein R$^{1b}$ is of following formula:

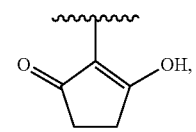

each of R$^3$ is independently selected from the group consisting of H, —OH and —OR$^w$, wherein R$^w$ is D-glucose;
each of R$^2$ and R$^4$, independently from each other and at each occurrence are selected from H or —OH;
each of R$^5$ is independently selected from the group consisting of H, —OH and —CH$_3$;
the Lipid is chosen among following Formula L$_1$ or Formula L$_2$:

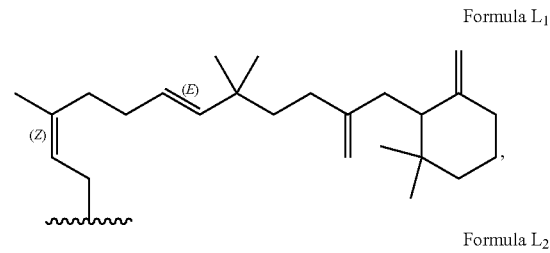

Formula L$_1$

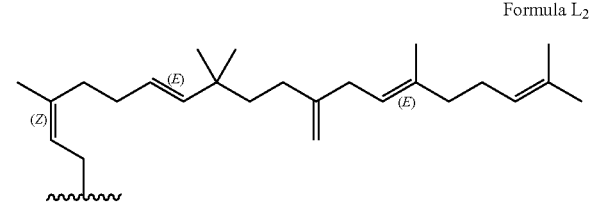

Formula L$_2$

More preferably, the anti-inflammatory compound (C) is a mixture of anti-inflammatory compounds (C) of class I, as detailed above.

Non limitative examples of commercially available anti-inflammatory compounds (C) suitable for the invention include Flavomycin®.

The commercially available Flavomycin® is also generally known under its synonym name Bambermycin.

Bambermycin or Flavomycin® is a known complex of compounds, primarily composed of moenomycins A and C, in particular the main compound is moenomycin A, according to formula (Ib) as detailed below, and the minor compounds are labeled as $A_{12}$, $C_1$, $C_3$ and $C_4$. Moenomycin A and the minor compounds, labeled as $A_{12}$, $C_1$, $C_3$ and $C_4$, are compounds according to formula (Ia), as detailed above.

In moenomycin A, according to formula (Ib) as detailed below, and the minor compounds $A_{12}$, $C_1$, $C_3$ and $C_4$, the Lipid is according to Formula $L_2$, $R^2$ is H, $R^1$ is —NH($R^{1b}$), wherein $R^{1b}$ is of following formula:

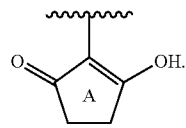

In moenomycin A, $R^3$ is $OR^w$, wherein $R^w$ is D-glucose, $R^4$ is OH and $R^5$ is $CH_3$. In moenomycin $A_{12}$, $R^3$ is $OR^w$, wherein $R^w$ is D-glucose, $R^4$ is H and $R^5$ is OH.

In moenomycin $C_1$, $R^3$ is H, $R^4$ is H and $R^5$ is OH. In moenomycin $C_3$, $R^3$ is H, $R^4$ is OH and $R^5$ is $CH_3$. In moenomycin $C_4$, $R^3$ is OH, $R^4$ is OH and $R^5$ is $CH_3$.

Bambermycin or Flavomycin® can be obtained from Streptomyces bambergiensis and Streptomyces ghanaensis Streptomyces ederensis, Streptomyces geysiriensis and related strains or biosynthesized thereby thus forming a complex of compounds, as discussed above. Since the complex is not extensively purified, Flavomycin® also contains building blocks ad various intermediates of the biosynthesis.

Bambermycin is also known as flavophospholipol. Bambermycin, flavophospholipol and Flavomycin® are used interchangeably herein.

A preferred anti-inflammatory compound (C) of class I is notably moenomycin A according to formula (Ib), or the pharmaceutically acceptable salt, pharmaceutically acceptable solvate, isomer or mixture thereof:

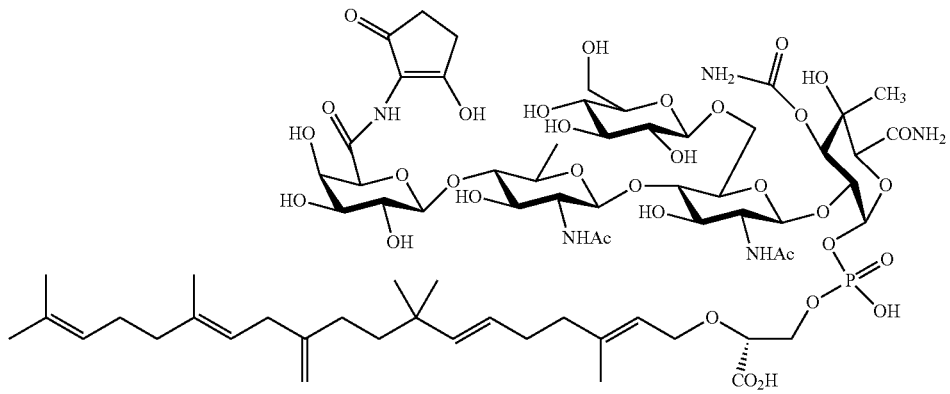

According to an alternative embodiment of the present invention, anti-inflammatory compounds (C) are compounds according to formula (IIa) [anti-inflammatory compounds (C) of class II, herein after] or the pharmaceutically acceptable salt, pharmaceutically acceptable solvate, isomer or mixture thereof:

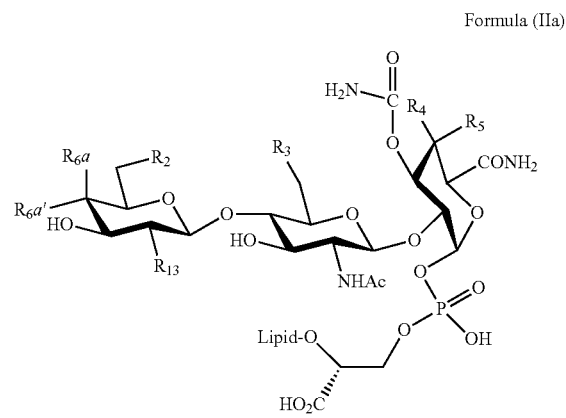

wherein
$R^3$ is H or —OH;
each of $R^2$ and $R^4$, independently from each other and at each occurrence, are selected from H or —OH;
each of $R^{6a}$ and $R^{6a'}$, independently from each other and at each occurrence, are selected from H or —OH, preferably $R^{6a}$ is H and $R^{6a'}$ is —OH;
$R^5$ is H, —OH or $CH_3$;
$R^{13}$ is —OH or —NHC(=O)$CH_3$
the Lipid is chosen among following Formula $L_3$, Formula $L_4$ or Formula $L_5$:

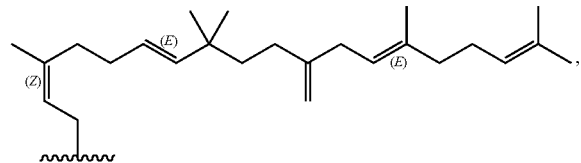

-continued

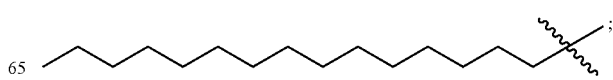

-continued

Formula L₅

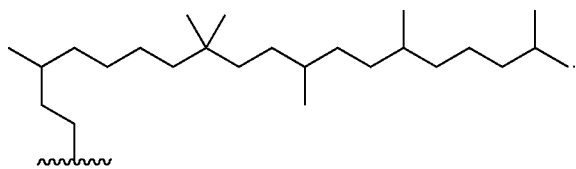

According to an alternative embodiment of the present invention, anti-inflammatory compounds (C) are compounds according to formula (IIIa) [anti-inflammatory compounds (C) of class III, herein after] or the pharmaceutically acceptable salt, pharmaceutically acceptable solvate, isomer or mixture thereof:

Formula (IIIa)

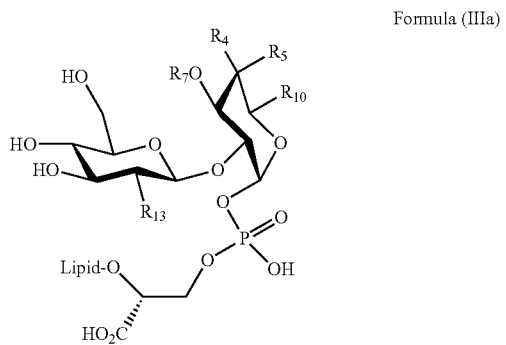

wherein
- each of $R^4$ and $R^5$, independently from each other and at each occurrence are selected from the group consisting of H, —CH₃ and —OH;
- $R_7$ is independently selected from H or —C(=O)NH₂, preferably, $R_7$ is C(=O)NH₂;
- $R^{10}$ is independently selected from —C(=O)NH₂ or —C(=O)OH, preferably, $R^{10}$ is C(=O)NH₂;
- $R^{13}$ is independently selected from the group consisting of —OH or —NHC(=O)CH₃, preferably $R^{13}$ is —NHC(=O)CH₃
- the Lipid is chosen among following Formula L₆, Formula L₇ or Formula L₈:

Formula L₆

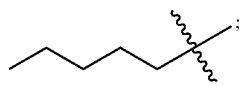

Formula L₇

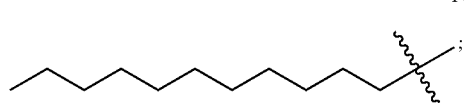

Formula L₈

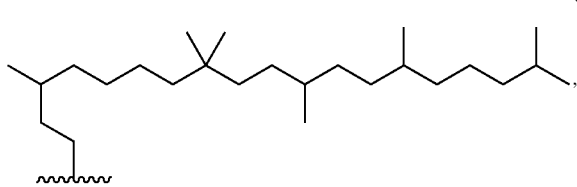

For therapeutic use, salts of the anti-inflammatory compound (C) of the present invention, as detailed above, are those wherein the counter-ion is pharmaceutically acceptable, which salts can be referred to as pharmaceutically acceptable acid and base addition salts. However, salts of acids and bases that are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable acid and base addition salts as mentioned hereinabove are meant to comprise the therapeutically active non-toxic acid and base addition salt forms that the anti-inflammatory compounds (C) of the present invention, as detailed above, are able to form. The pharmaceutically acceptable acid addition salts can conveniently be obtained by treating the base form with such appropriate acid in an anion form. Appropriate anions comprise, for example, trifluoroacetate, acetate, benzenesulfonate, benzoate, bicarbonate, bitartrate, bromide, calcium edetate, camsyiate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, and the like. The counterion of choice can be introduced using ion exchange resins. Conversely said salt forms can be converted by treatment with an appropriate base into the free base form.

The anti-inflammatory compounds (C) as specified herein, containing an acidic proton may also be converted into their nontoxic metal or amine addition salt forms by treatment with appropriate organic and inorganic bases in a cation form. Appropriate basic salts comprise those formed with organic cations such as benzathine, chloroprocaine, choline, diethanolamine, ethylenediamine, meglumine, procaine, and the like; and those formed with metallic cations such as aluminum, calcium, lithium, magnesium, potassium, sodium, zinc, and the like. Conversely said salt forms can be converted by treatment with an appropriate acid into the free form.

The term addition salt as used hereinabove also comprises the solvates which the anti-inflammatory compound (C), as specified herein, as well as the salts thereof, are able to form. Such solvates are for example hydrates, alcoholates and the like.

It is generally known that inflammatory-related diseases involve a sophisticated cytokine network "system", such that the functioning of the immune system is finely balanced by the activities of pro-inflammatory and anti-inflammatory mediators or cytokines.

As said, the anti-inflammatory compound (C) of the present invention, as detailed above, acts upon the inflammatory mechanisms in mammals. Preferably, the anti-inflammatory compound (C) of the present invention, as detailed above, acts upon the inflammatory mechanisms in non-human mammals. The non-human mammal may be a pig; a ruminant such as notably cattle, horses; a camel; a sheep; a goat; a cat; a dog; or a rodent such as notably a mouse, a rabbit or a rat; preferably a pig.

The Applicant has surprisingly found that the anti-inflammatory compound (C) of the present invention, as detailed above, can act upon the expression of at least one cytokine by suppressing or inhibiting the expression of the at least one cytokine wherein said cytokine is selected from the group consisting of pro-inflammatory cytokines, anti-inflammatory cytokines and chemokines.

Within the context of the present invention, the expressions "at least one cytokine" is intended to denote one or more than one cytokine. In other words, the anti-inflammatory compound (C) of the present invention can suppress or inhibit the expression of one, two, three or more cytokines at the same time thereby achieving better therapeutic efficacy with less side effects.

The Applicant has further found that by suppressing or inhibiting the expression of the at least one cytokine by the anti-inflammatory compound (C) of the present invention, a substantial decrease in the infiltration of macrophages, B-cells and T-cells was observed. This being said, the anti-inflammatory compound (C) of the present invention, shows inflammation suppressing or inhibiting properties.

Examples of illnesses, mediated by the cytokines (C), and which are treatable by the anti-inflammatory compound (C) of the present invention notably include inflammatory diseases and inflammatory-related diseases.

Non-limiting examples of inflammatory diseases notably include arthritis, rheumatoid arthritis, an inflammatory bowel disease, psoriasis, multiple sclerosis, Systemic Lupus Erythematosus (SLE), pancreatitis, scleroderma, diabetes type I, a gastrointestinal inflammatory disorder, allergic conjunctivitis, glomerulonephritis, Sjögren's syndrome, uvetitis, dermatitis, ankylosing spondylitis, and fibromyalgia.

It is understood that the term "gastrointestinal inflammatory disorder" refers to disorders such as acute gastritis, chronic gastritis, the development and recurrence of gastric ulcers, Crohn's disease, inflammatory bowel disease, irritable bowel syndrome and ulcerative colitis.

Non-limiting examples of inflammatory-related diseases notably include a neurodegenerative disorder, congestive heart failure, stroke, aortic valve stenosis, kidney failure, allergy, fibrosis, atherosclerosis, a metabolic disease, a cardiovascular disease, a chemotherapy/radiation related complication, a liver disease, a gastrointestinal disorder, an ophthamological disease, diabetic retinopathy, a pulmonary disorder, and leprosy.

The pro-inflammatory cytokines notably include IL-1α, IL-1β, IL-2, IL-3, IL-6, IL-7, IL-9, IL-12, IL-17, IL-18, IL-23,TNF-α, LT, LIF, Oncostatin, and IFN-α, IFN-β, and IFN-Υ.

The anti-inflammatory cytokines notably include IL-4, IL-10, IL-11, W-13 and TGF β.

The chemokines notably include IL-8, Gro-α, MIP-1, MCP-1, ENA-78, and RANTES.

Unless otherwise mentioned or indicated, the designation of the cytokines (C), as detailed above, encompasses the presence of all possible homologue forms, which said anti-inflammatory compounds (C) may suppress. Homology is defined as the relationship between biological structures, proteins or DNA sequences that are derived from a common ancestor. For example, the term "IL-8" refers to IL-8 and all homologues of IL-8, such as notably the IL-$8_{Kc}$, IL-$8_{MIP}$, IL-$8_{LIX}$ and the like.

Pharmaceutical Compositions

The present invention further relates to a pharmaceutical composition comprising a therapeutically effective amount of the anti-inflammatory compound (C) as defined above and as defined in any one of the embodiments presented herein, in particular the anti-inflammatory compound (C) of any of the classes (I) to (III), as defined above, and a pharmaceutically acceptable carrier.

In the rest of the text, the expression "the anti-inflammatory compound (C)" is understood, for the purposes of the present invention, both in the plural and the singular, that is to say that the inventive composition may comprise one or more than one anti-inflammatory compound (C)"

In still a further aspect, this invention relates to a process of preparing a pharmaceutical composition, as detailed above, which comprises intimately mixing a pharmaceutically acceptable carrier with a therapeutically effective amount of the anti-inflammatory compound (C), as defined above and as defined in any one of the embodiments presented herein, in particular an anti-inflammatory compound (C) of any of the classes (I) to (III), as defined above.

Therefore, the anti-inflammatory compounds (C) of the present invention, as specified herein, in particular the anti-inflammatory compounds (C) of any of the classes (I) to (III), as defined above, may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets.

Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations, which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The anti-inflammatory compound (C), as defined above and as defined in any one of the embodiments presented herein, in particular the anti-inflammatory compounds (C) of any of the classes (I) to (III), as defined above, may also be administered via oral inhalation or insufflation by means of methods and formulations employed in the art for administration via this way. Thus, in general the anti-inflammatory compound (C) as specified herein, in particular the anti-inflammatory compounds (C) of any of the classes (I) to (III), as defined above, may be administered to the lungs in the form of a solution, a suspension or a dry powder, a solution being preferred. Any system developed for the delivery of solutions, suspensions or dry powders via oral inhalation or insufflation are suitable for the administration of the present compounds.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

It is understood that the term "therapeutically effective amount" in general refers to that amount of the active compound or component or pharmaceutical agent that elicits the biological or medicinal response in a tissue, system, animal or human that is being sought, in the light of the present invention, by a researcher, veterinarian, medical doctor or other clinician, which includes alleviation of the symptoms of the disease being treated.

In the present invention, the therapeutically effective amount of the anti-inflammatory compound (C), as defined above, in particular the anti-inflammatory compound (C) of any of the classes (I) to (III), as defined above, is intended to refer to an amount sufficient to prophylactically act against, to stabilize or reduce illnesses mediated by the at least one cytokine selected from the group consisting of pro-inflammatory cytokines, anti-inflammatory cytokines and chemokines, as detailed above, in particular the at least one cytokine selected from the group consisting of IL-8, Gro-α, MIP-1, MCP-1, ENA-78, and RANTES, IL-1α, IL-1β, IL-2, IL-3, IL-6, IL-7, IL-9, IL-12, IL-17, IL-18, IL-23,TNF-α, LT, LIF, Oncostatin, IFN-α, IFN-β, IFN-ϒ, IL-4, IL-10, IL-11, W-13 and TGF β, more preferably the at least one cytokine is selected from the group consisting of IL-8, IL-4, IL-6, IL-10, TNF-α, TNF-β, IL-17, IL-23 and IFN-ϒ, even more preferably the at least one of said cytokine is selected from the group consisting of IL-8, IL-1β and IFN-ϒ.

The Anti-Inflammatory Compounds (C) and Pharmaceutical Compositions, Uses as Medicaments and in Treatments of Diseases The present invention relates to an anti-inflammatory compound (C), as defined above, in particular the anti-inflammatory compound (C) of any of the classes (I) to (III), as defined above, for use as a medicament.

The present invention also relates to a pharmaceutical composition comprising a therapeutically effective amount of the anti-inflammatory compound (C), as defined above and as defined in any one of the embodiments presented herein, in particular the anti-inflammatory compound (C) of any of the classes (I) to (III), as defined above, and a pharmaceutically acceptable carrier, for use as a medicament.

The present invention relates to an anti-inflammatory compound (C), as defined above, in particular an anti-inflammatory compound (C) of any of the classes (I) to (III), as defined above, for use in the treatment of inflammatory diseases selected from the group of arthritis, rheumatoid arthritis, an inflammatory bowel disease, psoriasis, multiple sclerosis, Systemic Lupus Erythematosus (SLE), pancreatitis, scleroderma, diabetes type I, a gastrointestinal inflammatory disorder, allergic conjunctivitis, glomerulonephritis, Sjögren's syndrome, uveitis, dermatitis, ankylosing spondylitis, and fibromyalgia, preferably for use in the treatment of gastrointestinal inflammatory disorders such as acute gastritis, chronic gastritis, the development and recurrence of gastric ulcers, Crohn's disease, inflammatory bowel disease, irritable bowel syndrome and ulcerative colitis, more preferably for use in the treatment of acute gastritis, chronic gastritis, the development and recurrence of gastric ulcers.

The present invention relates to an anti-inflammatory compound (C), as defined above, in particular an anti-inflammatory compound (C) of any of the classes (I) to (III), as defined above, for use in the treatment of inflammatory-related diseases selected from the group of a neurodegenerative disorder, congestive heart failure, stroke, aortic valve stenosis, kidney failure, allergy, fibrosis, atherosclerosis, a metabolic disease, a cardiovascular disease, a chemotherapy/radiation related complication, a liver disease, a gastrointestinal disorder, an ophthamological disease, diabetic retinopathy, a pulmonary disorder, and leprosy.

Consequently, the anti-inflammatory compound (C), as defined above, in particular the anti-inflammatory compound (C) of any of the classes (I) to (III), as defined above, and the pharmaceutical composition, as defined above, can be used in the manufacture of a medicament useful for treating, preventing or combating illness or disease associated with the expression of cytokines including inflammatory diseases, as defined above and inflammatory-related diseases, as defined above.

The present invention relates to an anti-inflammatory compound (C), as defined above, in particular an anti-inflammatory compound (C) of any of the classes (I) to (III), as defined above, for use in the treatment of a disease mediated by at least one cytokine.

The at least one cytokine is advantageously selected from the group consisting of pro-inflammatory cytokines, anti-inflammatory cytokines and chemokines, as detailed above, preferably the at least one cytokine is selected from the group consisting IL-8, Gro-α, MIP-1, MCP-1, ENA-78, and RANTES, IL-1α, IL-1β, IL-2, IL-3, IL-6, IL-7, IL-9, IL-12, IL-17, IL-18, IL-23,TNF-α, LT, LIF, Oncostatin, IFN-α, IFN-β, IFN-ϒ, IL-4, IL-10, IL-11, W-13 and TGF β, more preferably the at least one cytokine is selected from the group consisting of IL-8, IL-4, IL-6, IL-10, TNF-α, TNF-β, IL-17, IL-23 and IFN-ϒ, even more preferably the at least one of said cytokine is selected from the group consisting of IL-8, IL-1β and IFN-ϒ.

The exact dosage and frequency of administration depends on the particular anti-inflammatory compound (C) as specified herein, used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

As said above, the anti-inflammatory compound (C) of the present invention, as detailed above, may act upon the inflammatory mechanisms in animals.

For administration to animals, the anti-inflammatory compound (C), as defined above, in particular an anti-inflammatory compound (C) of any of the classes (I) to (III), as defined above, or the pharmaceutical composition thereof, comprising at least one of said anti-inflammatory compound (C) as active ingredient, may be added to the animal's feed or drinking water, may be administered through sprinkling, as a probiotic to a lactating dam may be administered as a slow-release bolus or via a licking stone.

The effective amount of the anti-inflammatory compound (C), as defined above, in particular the anti-inflammatory compound (C) of any of the classes (I) to (III), as defined above, that specifically suppresses or inhibits the expression of the at least one cytokine, as detailed above, for the treatment of animals is advantageously at least 1 ppm, preferably at least 2 ppm, more preferably at least 3 ppm, based on the total weight of the animal feed. On the other hand, the effective amount of the anti-inflammatory compound (C), as defined above, in particular the anti-inflammatory compound (C) of any of the classes (I) to (III), as defined above, the composition (C) is advantageously less than 130 ppm, preferably less than 70 ppm, more preferably less than 35 ppm, based on the total weight of the animal feed, the animal which in this case is a rodent, notably a mouse. it has to be understood that for the purpose of the present invention the upper limit is not critical and the effective amount depends on the particular species treated. The invention further relates to an animal feed comprising the anti-inflammatory compound (C), as defined above, in particular the anti-inflammatory compound (C) of any of the classes (I) to (III), as defined above, or the pharmaceutical composition thereof, comprising said anti-inflammatory compound (C) as active ingredient.

Methods for the Treatment of Inflammatory Diseases Using the Anti-Inflammatory Compounds (C)

The present invention relates to an in-vivo method of suppressing or inhibiting inflammatory responses by using at least one anti-inflammatory compound (C), as defined above, in particular the anti-inflammatory compound (C) of any of the classes (I) to (III), as defined above, and as defined in any one of the embodiments presented herein.

The present invention further relates to a method of suppressing or inhibiting the expression of at least one cytokine, in a mammal, said method comprising the administration to an mammal in need thereof, of an amount of anti-inflammatory compound (C), as defined above and as defined in any one of the embodiments presented herein, sufficient to inhibit or suppress at least one cytokine, wherein the cytokine is selected from the group consisting of IL-8, Gro-$\alpha$, MIP-1, MCP-1, ENA-78, and RANTES, IL-1$\alpha$, IL-1$\beta$, IL-2, IL-3, IL-6, IL-7, IL-9, IL-12, IL-17, IL-18, IL-23, TNF-$\alpha$, LT, LIF, Oncostatin, IFN-$\alpha$, IFN-$\beta$, IFN-$\Upsilon$, IL-4, IL-10, IL-11, W-13 and TGF $\beta$, more preferably the at least one cytokine is selected from the group consisting of IL-8, IL-4, IL-6, IL-10, TNF-$\alpha$, TNF-$\beta$, IL-17, IL-23 and IFN-$\Upsilon$, even more preferably the at least one of said cytokine is selected from the group consisting of IL-8, IL-$\beta$ and IFN-$\Upsilon$.

The present invention further relates to a method of treating inflammatory-related diseases associated with cytokine expression levels in mammals, said method comprising the administration to a mammal in need thereof of an amount of anti-inflammatory compound (C) as defined above and as defined in any one of the embodiments presented herein, sufficient to treat said inflammatory-related disease. The following examples are merely illustrative of some non-limiting embodiments of the present invention.

EXAMPLES

Materials a) Experimental Set-Up

Experiments were conducted to evaluate the effects of feed supplementation with Flavomycin® as anti-inflammatory compound (C) in a mouse model.

For the in-vivo experiments, the BALB/c mouse strain was chosen for its association with a more pronounced gastric pathology compared to other mouse strains. The mice were divided in 4 groups of 8 animals each. The 4 groups have following characteristics:

1) Infected+Standard Diet: Comparative Example 1

The 'comparative example 1' group of mice was twice intragastrically inoculated with $10^8$ viable bacteria of the *Helicobacter Suis* (*H. suis*) HS1 strain within a 48 hours interval (at day 8 and day 9). At day 17, the mice were fed ad libitum with a control diet (standard diet without Flavomycin®). After 73 days, the mice were euthanized by cervical dislocation under deep isoflurane anesthesia. A strip of gastric tissue was taken to perform the experimental procedures as detailed below.

2) Infected+Flavomycin® Supplemented Diet (Flavomycin® Amount <100 ppm Based on Total Amount of the Given Food): Example 1

The 'example 1' group of mice was twice intragastrically inoculated with $10^8$ viable bacteria of the HS1 (*H. suis*) strain within a 48 hours interval (at day 8 and day 9). At day 17, the mice were fed ad libitum with a Flavomycin® supplemented diet (amount of Flavomycin® <100 ppm based on total amount of diet). After 73 days, the mice were euthanized by cervical dislocation under deep isoflurane anesthesia. A strip of gastric tissue was taken to perform the experimental procedures as detailed below.

3) Uninfected+Standard Diet: Comparative Example 2

The 'comparative example 2' group of mice did not receive intragastrical inoculation and was fed ad libitum with the control feed, a standard diet withoutFlavomycin®. After 73 days, the mice were euthanized by cervical dislocation under deep isoflurane anesthesia. A strip of gastric tissue was taken to perform the experimental procedures as detailed below.

4) Uninfected+Flavomycin® Supplemented Diet (Flavomycin® Amount Amount <100 ppm Based on Total Amount of the Given Food): Example 2

The 'example 2' group of mice did not receive intragastrical inoculation and was fed ad libitum with a Flavomycin® supplemented diet (amount of Flavomycin® <100 ppm based on total amount of diet). After 73 days, the mice were euthanized by cervical dislocation under deep isoflurane anesthesia. A strip of gastric tissue was taken to perform the experimental procedures as detailed below.

b) Verification of Experimental Setup—*H. suis* Quantification

The presence of infection with *H. suis* was determined via qRT-PCR experiments. The experiments were conducted as detailed below. In Table 1 it is demonstrated that the groups 'comparative example 1' and 'example 1' are successfully infected with the *H. suis* bacteria. The groups 'comparative example 2' and 'example 2' are uninfected as shown in Table 1 since no *H. suis* bacteria have been detected in these animals.

TABLE 1

Determination of the presence of infection with *H. suis* via qRT-PCR experiments, expressed in Log ratio's of *H. Suis* per mg Tissue (absolute quantification of nucleic acid (amount of bacterial DNA) per given amount of sample (mg tissue).

| EXAMPLE | LOG OF *H. suis*/MG TISSUE |
|---|---|
| Comparative example 1 | 7.880 |
| Example 1 | 36.900 |
| Comparative example 2 | 0 |
| Example 2 | 0 |

METHODS qRT-PCR Assay

1) *H. suis* Quantification

The quantification of *H. suis* colonization in the stomach was carried out based on the publications of Blaecher C. et al. (2013) and O'Rourke J. L. et al. (2004).

The presence of *H. suis* DNA in the extracts was determined using an *H. suis*-specific qRT-PCR with absolute quantification, based on the ureA gene (Blaecher C. et al. (2013)). First, the standard was generated by amplifying a part of the ureAB gene cluster (1236 bp) from *H. suis* strain HS5 using primers U430F and U1735R (O'Rourke J. L. et al. (2004)). In brief, PCR amplification reactions involved 1×reaction buffer [67 mM Tris/HCl, 16 mM (NH 4) 2SO4, 0.45% Triton X-100, 0.2% gelatin], one unit of Taq DNA polymerase (Biotech International), 200 µM of each deoxynucleotide triphosphate, 2 mM MgCl 2, 10 pmol of each oligonucleotide primer and 1 µl diluted DNA (usually a 1:10 dilution of original sample containing approximately 20-100 ng µl--1) in a final volume of 50 µl. The cycling conditions were initial denaturation at 94° C. for 3 min, then 35 cycles of 94° C. for 10 s, 52° C. for 30 s and 72° C. for 1.5 min, followed by a final extension step of 72° C. for 5 min. All reactions were carried out using a Perkin Elmer PE2400 thermocycler. PCR products were separated on agarose mini-gels in TAE buffer (40 mM Tris/acetate, 1 mM EDTA) and photographed under UV transillumination after staining with ethidium bromide. PCR products were purified prior to sequencing with Wizard PCR Preps DNA Purification System (Promega) or Centricon-100 filters (Amicon). The amplified DNA was then directly sequenced using the ABI PRISM Ready Reaction DyeDeoxy Terminator Cycle Sequencing Kit (PE Applied Biosystems) and the GeneAmp® PCR System 2400 (Perkin Elmer) according to the manufacturers' protocols. Sequencing products were separated on model 377 DNA Sequencer machines and analysed using programs contained in the inherit package (PE Applied Biosystems). In all cases both strands of DNA were sequenced with contiguous overlaps. After generating the standard, 10-fold dilutions were made, starting at 108 PCR amplicons, for each 9 µL of reaction mixture. One microlitre of extracted DNA template was added to 9 µL reaction mixture, consisting of 0.25 µL of both primers located within the 1236 bp fragment (to yield a 150 bp PCR product), 3.5 µL HPLC water and 5 µL SensiMix™ SYBR No-ROX (Bioline Reagents Ltd, London, UK). Sense primer was BF_HsuisF1: 5'-AAA ACA MAG GCG ATC GCC CTG TA-3'. Anti-sense primer was BF_Hsuis R1: 5'-TTT CTT CGC CAG GTT CAA AGC G-3'. Annealing temperature was 62 ° C. Both standards and samples were run in duplicate on a CFX96™ RT-PCR System with a C1000 Thermal Cycler (Bio-Rad, Hercules, CA, USA). The results are expressed in terms of the absolute quantification of nucleic acid (amount of bacterial DNA) per given amount of sample (mg tissue).

2). Cytokine Expression Levels

An qRT-PCR to evaluate cytokine expression levels was performed based on the publications of Flahou B. et al. (2012) and Liu C. et al. (2016). RNA was extracted using the RNeasy Mini Kit® (Qiagen, Hilden, Germany), according to the manufacturer's instructions. The obtained RNA concentrations were measured using a NanoDrop® spectrophotometer (Isogen Life Science, Utrecht, The Netherlands), after which the concentration of all samples obtained from all mice belonging to the 4 groups, as defined above in the experimental set-up. was adjusted to 1 µg/µL, followed by cDNA synthesis using the iScript™ cDNA Synthesis Kit (Bio-Rad, California, USA). Expression analysis was then performed for genes encoding host factors involved in inflammation. The housekeeping genes PPIa, H2afz, and HPRT were included as reference genes. All primer sequences used are shown in Table 2. The mRNA expression levels of the reference and target genes were quantified using a RT-PCR, as described earlier (Flahou B. et al. (2012)). No-template-control reaction mixtures were included and all said samples were run in duplicate. The threshold cycle values (Ct)-values were first normalized to the geometric mean of the Ct-values from the reference genes. Fold changes were calculated using ΔΔCT method (72) with mean of Ct-values from the *H. suis* negative mice. Finally, for each target gene, the results were expressed as fold changes of the mRNA expression of *H. suis* positive mice relative to mRNA expression levels of *H. suis* negative mice. The results are summarized in Tables 3 and 4, below.

TABLE 2

Primer sequences used in the qRT-PCR method

| SEQUENCE (5'-3') | PRIMER |
|---|---|
| CTGACCTAGAGAAGACACAT | IFN-γ-FORWARD |
| GGTCAGTGAAGTAAAGGTAC | IFN-γ-REVERSE |
| CACCTCACAAGCAGAGCACAAG | IL-1β-FORWARD |
| GCATTAGAAACAGTCCAGCCCATAC | IL-1β-REVERSE |
| TGCCTGAAGACCCTGCCAAGG | IL-8$_{MIP}$-FORWARD |
| GTTAGCCTTGCCTTTGTTCAG | IL8$_{MIP}$-REVERSE |
| | HOUSEKEEPING GENES |
| GGTATCACCCCTCGTCACTT | H2$_{AFZ}$-FORWARD |
| TCAGCGATTTGTGGATGTGT | H2$_{AFZ}$-RESEVERSE |
| CAGGCCAGACTTTGTTGGAT | HPRT-FORWARD |
| TTGCGCTCATCTTAGGCTTT | HPRT-REVERSE |
| AGCATACAGGTCCTGGCATC | PPI$_A$-FORWARD |
| TTCACCTTCCCAAAGACCAC | PPI$_A$-REVERSE |

Immunohistochemistry Experiments—Determination of T-Cell, B-Cell, Parietal Cell, Necrotic Cells and Macrophage Infiltration Immunohistochemistry was carried out based on the publication of Flahou B. et al. (2010). Consecutive sections of 5 μm were cut from the paraffin embedded tissues. After rehydration and deparaffinization, heat-induced antigen retrieval was performed in citrate buffer (pH 6.0) using a microwave oven. Slides were incubated with 3% $H_2O_2$ in methanol (5 min) and 30% goat serum (30 min) to block endogenous peroxidase activity and non-specific reactions, respectively. The differentiation between T and B lymphocytes was carried out by staining of CD3 and CD20 antigens. CD3 antigens were detected using a polyclonal rabbit anti-CD3 antibody (1/100; DakoCytomation). CD20 antigens were detected usinga polyclonal rabbit anti-CD20 antibody (1/100; Thermo Scientific, Fremont, USA), respectively. Incubation with primary antibodies directed against CD3 and CD20 was followed by incubation with a biotinylated goat anti-rabbit IgG antibody (1/500; DakoCytomation). After rinsing, the sections were incubated with a streptavidin-biotin-HRP complex (DakoCytomation) and the colour was developed with diaminobenzidine tetrahydrochloride (DAB) and $H_2O_2$. A primary antibody directed against the F4/80 surface marker (1/50; Santa Cruz Biotechnology, Inc., Santa Cruz, USA) was used for highlighting mature macrophages. Detection was done using a rat ABC staining system (Santa Cruz Biotechnology, Inc.). Apoptotic cells were identified by immunohistochemical staining using a rabbit polyclonal antibody directed against active caspase-3 and an anti-rabbit HRP-AEC cell and tissue staining kit (R&D Systems, Minneapolis, USA). Parietal cells were identified by immunohistochemical staining for the hydrogen potassium ATPase using a mouse monoclonal antibody (1/200; Abcam Ltd, Cambridge, UK) and a biotinylated goat anti-mouse IgG antibody (1/200; DakoCytomation). Apoptotic cells were identified by immunohistochemical staining using a rabbit polyclonal antibody directed against active caspase-3 and an anti-rabbit HRP-AEC cell and tissue staining kit (R&D Systems, Minneapolis, USA). Parietal cells were identified by immunohistochemical staining for the hydrogen potassium ATPase using a mouse monoclonal antibody (1/200; Abcam Ltd, Cambridge, UK) and a biotinylated goat anti-mouse IgG antibody (1/200; DakoCytomation) Finally, positive cells were counted in five randomly chosen High Power Fields (magnification: ×400). An average of the positive cell count was then determined for each mouse. All the results are demonstrated in Tables 5, 6, 7, and 8.

RESULTS

Experiment 1

Measurement of cytokine expression levels in *H. suis* infected animals by using the qRT-PCR method as detailed above.

TABLE 3

Results of qRT-PCR experiment to determine effect of Flavomycin ® supplementation on cytokine levels in *H. Suis* infected animals expressed as the fold change in mRNA expression levels.

| | Expression (fold change) | |
|---|---|---|
| Cytokine | Comparative example 1 | Example 1 |
| IL - 1β | 0.82 | −1.38 |
| IL-8MIP | 2.65 | 1.60 |
| IFN-Υ | 2.15 | −3.88 |

Table 3 shows decreased expression levels of IL-1β, IL-8MIP and IFN-Υ in the infected animals receiving a Flavomycin® supplemented diet (example 1) compared to the control group on a standard diet (comparative example 1).

Experiment 2

Measurement of cytokine expression levels in the absence of *H. suis* infection by using the qRT-PCR method as detailed above.

TABLE 4

Results of qRT-PCR experiment to determine effect of Flavomycin ® supplementation on cytokine levels in uninfected animals, expressed as the fold change in mRNA expression levels.

| | Expression (fold change) | |
|---|---|---|
| Cytokine | Comparative example 2 | Example 2 |
| IL - 1β | 1.08 | −1.42 |
| IL-8MIP | 2.47 | 2.34 |
| IFN-Υ | 1.25 | 1.99 |

Table 4 shows a decreased expression of IL-1β even in the absence of infection. IL-8MIP expression levels stay stable, while there is a small increase in the expression of IFN-Υ.

Experiment 3

Evaluation of inflammatory response in *H. suis* infected animals by using immunohistochemistry experiments, as detailed above.

TABLE 5

Results of immunohistochemistry experiments to determine the effect of Flavomycin ® supplementation on the number of infiltrating T-cells, B-cells and macrophages in H. Suis infected animals, expressed as the average number of positive cells counted.

| Inflammatory parameter | Comparative example 1 | Example 1 |
|---|---|---|
| T-cells | 60.28 | 21.38 |
| B-cells | 3.08 | 0.48 |
| Macrophages | 4.75 | 1.35 |

Table 5 shows a strong reduction in the number of infiltrating T-cells, B-cells and macrophages in mice infected with H. suis and treated with Flavomycin® (example 1) compared to the comparative example 1.

Experiment 4

Evaluation of inflammatory response in the absence of H. suis infection by using immunohistochemistry experiments, as detailed above.

TABLE 6

Results of immunohistochemistry experiments to determine the effect of Flavomycin ® supplementation on the number of infiltrating T-cells, B-cells and macrophages uninfected animals, expressed as the average number of positive cells counted.

| Inflammatory parameter | Comparative example 2 | Example 2 |
|---|---|---|
| T-cells | 54.00 | 14.10 |
| B-cells | 0.85 | 1.65 |
| Macrophages | 1.15 | 0.18 |

Table 6 shows an anti-inflammatory effect of Flavomycin® for the group of uninfected mice receiving a supplemented diet (example 2) compared to comparative example 2. In particular a decrease in T-cells and macrophages was observed.

Taking the results from experiments 3 and 4 together, Flavomycin® has been shown to have an anti-inflammatory capacity irrespective of an infection with H. suis.

Experiment 5

Physiological evaluation of H. suis infected animals by using immunohistochemistry experiments, as detailed above.

TABLE 7

Results of immunohistochemistry experiments to determine the effect of of Flavomycin ® supplementation on the number of necrotic and parietal cells in H. Suis infected animals, expressed as the average number of positive cells counted.

| Physiological parameter | Comparative example 1 | Example 1 |
|---|---|---|
| Necrotic cells | 0.95 | 0.50 |
| Parietal cells | 151.25 | 213.25 |

Table 7 shows a reduction in the number of necrotic cells for the infected group receiving a diet supplemented with of Flavomycin® (example 1) in comparison with comparative example 1. This indicates that the animals receiving a Flavomycin® supplemented diet experience less cell necrosis, which can be explained by the suppression of inflammatory responses. For the number of parietal cells there is a higher number of cells measured in the group receiving a diet supplemented with Flavomycin®. This can be explained by the fact that the reduction of inflammation, due to the administration of Flavomycin®, causes less damage to the parietal cells of the stomach.

Experiment 6

Physiological evaluation of animals without H. suis infection by using immunohistochemistry experiments, as detailed above.

TABLE 8

Results of immunohistochemistry experiments to determine the effect of Flavomycin ® supplementation on the number of necrotic and parietal cells in uninfected animals, expressed as the average number of positive cells counted.

| Physiological parameter | Comparative example 2 | Example 2 |
|---|---|---|
| Necrotic cells | 2.18 | 0.60 |
| Parietal cells | 214.63 | 211.38 |

Table 8 shows a reduction in the number of necrotic cells which is a result of the reduced inflammation. The number of parietal cells is approximately the same in example 2 and comparative example 2. This indicates that the treatment with Flavomycin does not negatively impact the number of parietal cells.

Taking all results together, the administration of Flavomycin® shows an anti-inflammatory effect since B-cell, T-cell and macrophage infiltration, as well as IL-1β, IL-8MIP, and IFN-ϒ levels were reduced in the groups of animals receiving a Flavomycin® supplemented diet. Moreover, it is shown that the anti-inflammatory effects are independent from H. suis infection.

The invention claimed is:

1. A method of treatment of an inflammatory disease or inflammatory-related disease in a mammal comprising administering an effective amount of an anti-inflammatory compound (C) according to general formula (Ib) herein, or a pharmaceutically acceptable salt, solvate, isomer, or mixture thereof, to a mammal in need thereof, wherein the inflammatory disease or inflammatory-related disease is not driven by a microbial infection, wherein the inflammatory disease or inflammatory-related disease is a gastrointestinal inflammatory disorder selected from the group consisting of: acute gastritis, chronic gastritis, the development and recurrence of gastric ulcers, Crohn's disease, inflammatory bowel disease, irritable bowel syndrome, and ulcerative colitis, and wherein said anti-inflammatory compound (C) acts upon inflammatory mechanisms in mammals

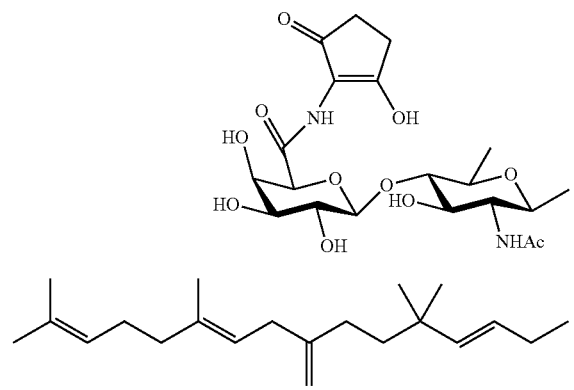

Formula (Ib)

-continued

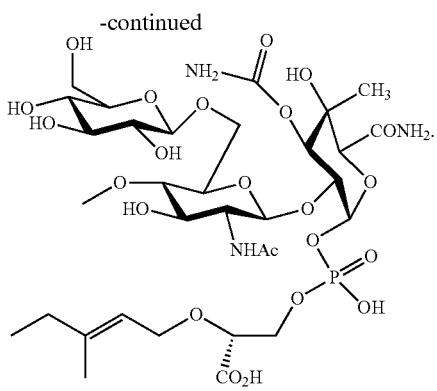

2. The method according to claim 1, wherein said anti-inflammatory compound (C) acts upon the inflammatory mechanisms in non-human mammals.

3. The method of claim 2, wherein the non-human mammal is a pig; a ruminant, a horse, a camel, a sheep, a goat, a cat, a dog, or a rodent.

4. The method according to claim 1, wherein said anti-inflammatory compound (C) acts upon the expression of at least one cytokine by suppressing or inhibiting the expression of the at least one cytokine wherein said cytokine is selected from the group consisting of pro-inflammatory cytokines, anti-inflammatory cytokines, and chemokines.

5. The method of claim 4, wherein the pro-inflammatory cytokine is IL-1β.

6. The method according to claim 1, wherein said inflammatory disease or inflammatory-related disease is mediated by at least one cytokine.

7. The method according to claim 6, wherein the at least one cytokine is IL-1β.

8. The method according to claim 1, wherein the anti-inflammatory compound (C) is in the form of a pharmaceutical composition comprising a therapeutically effective amount the anti-inflammatory compound (C) and a pharmaceutically acceptable carrier.

9. The method of claim 8, wherein the pharmaceutical composition is present in unit dosage form suitable for administration orally, rectally, percutaneously, or by parenteral injection, and wherein the unit dosage form is selected from the group consisting of tablets, capsules, pills, suppositories, powder packets, wafers, injectable solutions, suspensions, and segregated multiples thereof.

10. A method of suppressing or inhibiting the expression of at least one cytokine, in a mammal, comprising administering an effective amount of at least one anti-inflammatory compound (C) to a mammal in need thereof, wherein the amount of the compound (C) administered is sufficient to inhibit or suppress at least one cytokine, wherein said cytokine expression is not driven by a microbial infection, and is IL-1β, wherein the compound (C) is as defined according to claim 1.

* * * * *

SEQUENCE LISTING

```
<160> NUMBER OF SEQ ID NOS: 14

<210> SEQ ID NO 1
<211> LENGTH: 23
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(23)
<223> OTHER INFORMATION: BF_HsuisF1
```

```
<400> SEQUENCE: 1
aaaacamagg cgatcgccct gta                                              23

<210> SEQ ID NO 2
<211> LENGTH: 22
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(22)
<223> OTHER INFORMATION: BF_HsuisR1

<400> SEQUENCE: 2
tttcttcgcc aggttcaaag cg                                               22

<210> SEQ ID NO 3
<211> LENGTH: 20
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(20)
<223> OTHER INFORMATION: IFN-gamma - forward

<400> SEQUENCE: 3
ctgacctaga gaagacacat                                                  20

<210> SEQ ID NO 4
<211> LENGTH: 20
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(20)
<223> OTHER INFORMATION: IFN - gamma - reverse

<400> SEQUENCE: 4
ggtcagtgaa gtaaaggtac                                                  20

<210> SEQ ID NO 5
<211> LENGTH: 22
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(22)
<223> OTHER INFORMATION: IL-1beta - forward

<400> SEQUENCE: 5
cacctcacaa gcagagcaca ag                                               22

<210> SEQ ID NO 6
<211> LENGTH: 25
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(25)
<223> OTHER INFORMATION: IL-1beta - reverse
```

<400> SEQUENCE: 6
gcattagaaa cagtccagcc catac                                                       25

<210> SEQ ID NO 7
<211> LENGTH: 21
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(21)
<223> OTHER INFORMATION: IL-8MIP - forward

<400> SEQUENCE: 7
tgcctgaaga ccctgccaag g                                                           21

<210> SEQ ID NO 8
<211> LENGTH: 21
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(21)
<223> OTHER INFORMATION: IL-8MIP - reverse

<400> SEQUENCE: 8
gttagccttg cctttgttca g                                                           21

<210> SEQ ID NO 9
<211> LENGTH: 20
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(20)
<223> OTHER INFORMATION: H2AFZ - forward

<400> SEQUENCE: 9
ggtatcaccc ctcgtcactt                                                             20

<210> SEQ ID NO 10
<211> LENGTH: 20
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(20)
<223> OTHER INFORMATION: H2AFZ - reverse

<400> SEQUENCE: 10
tcagcgattt gtggatgtgt                                                             20

<210> SEQ ID NO 11
<211> LENGTH: 20
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(20)

```
<223> OTHER INFORMATION: HPRT - forward

<400> SEQUENCE: 11
caggccagac tttgttggat                                           20

<210> SEQ ID NO 12
<211> LENGTH: 20
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(20)
<223> OTHER INFORMATION: HPRT - reverse

<400> SEQUENCE: 12
ttgcgctcat cttaggcttt                                           20

<210> SEQ ID NO 13
<211> LENGTH: 20
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(20)
<223> OTHER INFORMATION: PPIA - forward

<400> SEQUENCE: 13
agcatacagg tcctggcatc                                           20

<210> SEQ ID NO 14
<211> LENGTH: 20
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(20)
<223> OTHER INFORMATION: PPIA - reverse

<400> SEQUENCE: 14
ttcaccttcc caaagaccac                                           20
```